United States Patent [19]

Zielenski

[11] Patent Number: 6,162,615
[45] Date of Patent: Dec. 19, 2000

[54] STABILIZED COENZYME SOLUTIONS AND THEIR USE THEREOF FOR THE DETERMINATION OF DEHYDROGENASES OR THE SUBSTRATE THEREOF IN AN ALKALINE MEDIUM

[75] Inventor: Ralf Zielenski, Benediktbeuern, Germany

[73] Assignee: Roche Diagnostics GmbH, Mannheim, Germany

[21] Appl. No.: 08/860,731

[22] PCT Filed: Nov. 20, 1996

[86] PCT No.: PCT/EP96/05107

§ 371 Date: Oct. 16, 1997

§ 102(e) Date: Oct. 16, 1997

[87] PCT Pub. No.: WO97/19190

PCT Pub. Date: May 29, 1997

[30] Foreign Application Priority Data

Nov. 22, 1995 [DE] Germany ............................ 195 43 493

[51] Int. Cl.[7] ............................ C12Q 1/32; A61K 33/24; H01B 1/12; C07H 19/207
[52] U.S. Cl. ................................ 435/26; 435/18; 435/25; 424/617; 424/618; 424/630; 424/646; 252/519.3; 252/519.32; 252/519.5; 252/520.3; 252/521.2; 436/79; 436/80; 436/81; 436/84; 536/26.24; 536/26.25
[58] Field of Search .................................. 435/26, 25, 18; 424/617, 618, 630, 646; 252/519.3, 519.32, 519.5, 520.3, 521.2; 436/79, 80, 81, 84; 536/26.24, 26.25

[56] References Cited

U.S. PATENT DOCUMENTS

| 3,331,752 | 7/1967 | Struck et al. ............................ 435/26 |
| 4,162,194 | 7/1979 | Pierre et al. ............................ 435/15 |
| 5,036,000 | 7/1991 | Palmer et al. ............................ 435/26 |

OTHER PUBLICATIONS

Green et al, Can. J. Biochem. 57:995–999 (1979).

*Primary Examiner*—Francisco Prats
*Attorney, Agent, or Firm*—Arent Fox Kintner Plotkin & Kahn, PLLC

[57] ABSTRACT

Stabilized aqueous coenzyme solutions which contain up to ca. 60 mM of a heavy metal salt and optionally a complexing agent in a defined ratio to the heavy metal salt as well as their use for the determination of dehydrogenases in particular lactate dehydrogenase or corresponding substrates in an alkaline environment.

59 Claims, No Drawings

STABILIZED COENZYME SOLUTIONS AND THEIR USE THEREOF FOR THE DETERMINATION OF DEHYDROGENASES OR THE SUBSTRATE THEREOF IN AN ALKALINE MEDIUM

The invention concerns stabilized aqueous solutions of a coenzyme for hydrogen-transferring enzymes as well as their use for determining a corresponding analyte (substrate) in a reduced form or the enzyme activity of a corresponding dehydrogenase. The stabilized solution contains a heavy metal salt and optionally a completing agent as a further component and hence enables the determination in an alkaline environment preferably at a pH value of 8.5 to 10.0.

The determination of enzyme activities (or substrate concentrations) in particular in blood serum or blood plasma plays an important role in clinical chemical diagnostics. Test procedures are often used for this which are based on the reduction of nicotinamide adenine dinucleotide ("NAD") or nicotinamide adenine dinucleotide phosphate ("NADP") and the photometric detection of the change of absorbance behaviour in the ultraviolet wavelength range ($\lambda$=334, 340 or 365 nm) which occurs in this process. When choosing suitable test conditions this change is linearly proportional to the enzyme activity (or substrate concentration) to be determined.

The method described in Eur. J. Chin. Chem. Chin. Biochem. 31, 897 (1994) and Eur. J. Chin. Chem. Chin. Biochem. 32, 639 (1994) is nowadays generally recommended to determine the enzyme activity of for example lactate dehydrogenase (LDH, E.C.1.1.1.27). The test principle is that lactate is oxidized to pyruvate with the simultaneous reduction of a coenzyme such as NAD or NADP to NADH or NADPH. Such a conversion, which in this case is for example catalysed by LDH, takes place in an alkaline medium (pH 9.4) i.e. under conditions under which it is known that NAD or NADP is unstable. This instability is manifested by a relatively rapid increase in absorbance (the so-called reagent blank) in the relevant wavelength range for the measurement so that the reagent combination already becomes useless after a short period (3 months) even with refrigerated storage (2° to 8° C.). This is a particular problem for the production of ready-to-use liquid reagents with long-term stability which are intended to enable the user to carry out analyses in the daily routine as simply and reliably as possible.

A process for stabilizing aqueous coenzymes using chelating agents and azides is known from JP 84/82398. However, a disadvantage of this process is that it is necessary to add azide which on the one hand has been classified as cancerogenic and in addition has an inhibitory effect on many enzymes. Moreover this stabilization process has clear limits at higher pH values and temperatures.

The object of the present invention is therefore to provide an improved stable liquid reagent containing a coenzyme for hydrogen-transferring enzymes which is suitable for the determination of dehydrogenase activity or of corresponding substrates.

The invention is achieved by an aqueous solution which contains a heavy metal salt at a concentration of approximately 1 to 60 mM preferably at a concentration of 2 to 10 mM. The pH value of corresponding working solutions is in the alkaline range preferably above pH 8.5, particularly preferably between pH 8.5 and 10.0. Working solutions are understood according to the invention to mean that the stabilized coenzyme solution is mixed with a solution which is essentially composed of a substance buffering in the alkaline range. It has proven to be advantageous that the ratio of stabilizer to buffer solution is ca. 1:5. Water-soluble salts of acids with heavy metal ions such as e.g. $Cu^{2+}$ and/or $Co^{2+}$ and also other heavy metals such as for example iron, manganese, zinc, nickel, silver, magnesium, calcium or palladium have proven to be suitable as the heavy metal salt. The acid residues of common acids known to a person skilled in the art come into consideration as the counterion i.e. the so-called acid anion such as for example sulfate, phosphate, the acid residues of carboxylic acids and halogenides. Copper and cobalt sulfate and/or the corresponding chlorides have proven to be particularly suitable.

Substances which are suitable as buffers are those which have a good buffering capacity between ca. 8.5 and 10.0 such as for example the so-called Good buffers (tricine, bicine, TAPS, AMPSO, CHES, CAPSO, AMP, CAPS), carbonates of alkaline metal ions, MEG, TRIS as well as borate or phosphate buffer. Mixtures of the said buffer substances have also proven to be suitable for the solution according to the invention. It has proven to be suitable when the buffer concentration is between 10 and 1000 mM particularly preferably between 400 and 600 mM.

The stability of the solutions can moreover be further improved when the solution additionally contains a complexing agent i.e. a ligand which has two or more coordination positions. In this case bidentate ligands such as e.g. ethylene diamine and quadridentate and multidentate ligands such as ethylene diamine-N,N,N,N-tetraacetic acid (EDTA) and respective salts in particular the disodium salt, crown ethers or cryptands have proven to be advantageous. It was possible to observe the stabilizing effect especially when the complexing agent is added in a particular ratio to the concentration of the heavy metal salt, the respective heavy metal salt being present in excess. The ratio of metal ion to complexing agent is preferably 2 to 1. This corresponds to a concentration of the complexing agent of approximately 0.5 to 30 mM preferably of 1.0 to 5.0 mM.

Coenzymes which come into consideration as coenzymes within the sense of the present invention are in particular NAD or NADP but also modified coenzymes such as for example thioNAD(P) or NHxDP (=nicotinamide hypoxanthine-dinucleotide phosphate). The coenzymes can be present at a concentration of about 1.0 to 60 mM, a range of 5.0 to 15.0 mM is preferred in this case.

The stabilized coenzyme solutions i.e. together with a heavy metal salt alone as well as together with a complexing agent, are preferably used in the form of lyophilisates. However, the ready-to-use reagent is also additonally stable over a long period as a granulate, powder mixture as well as an aqueous solution. Thus at temperatures of 2° to 8° C. no manifestations of decomposition of the reagent are found at all within 15 months. Under stress i.e. at a temperature of ca. 35° C. for 2 weeks and subsequent treatment at ca. 42° C. for one day it was possible to show that the solution containing the heavy metal salt remained unchanged up to approximately 60 mM i.e. remained stable.

A further subject matter of the invention is a method for the determination of a hydrogen-transferring analyte or a corresponding dehydrogenase in the presence of a hydrogen accepting coenzyme wherein the coenzyme is present in a stabilized aqueous alkaline solution as described above. The final concentration of the heavy metal salt in the test is in this case preferably between 0.1 and 1.0 mM; the final concentration of the optionally added complexing agent is preferably ca. 0.05 to 5 mM.

The determination is carried out especially in samples of biological origin such as for example whole blood, serum or plasma or milk or other human or animal sources or in plant extracts. The sample can be prepared with physiological saline. In such a case a 0.9% NaCl solution serves as a control value.

In the case that it is intended to determine the enzyme activity of a dehydrogenase such as for example lactate dehydrogenase, a substrate solution, for example a lactate solution, is used in a substance (mixture) buffering at ca. pH 9.4 (37° C). In this case the substrate can be used in the usual concentrations known to a person skilled in the art preferably in a range of 40 to 80 mM.

In order to determine a hydrogen-transferring analyte such as for example lactate, the respective dehydrogenase such as for example LDH is added first in a substance buffering between pH 8.5 and 10.0. As a rule dehydrogenase in an amount of approximately 70 to 500 U/l preferably of 110 to 220 U/l is adequate. The determination is usually carried out at ca. 37° C.

In addition to lactate which is quoted as an example it is also possible to determine in a similar manner glutamate or ammonia, alcohol, glyceraldehyde-3-phosphate, glucose or other parameters which can be converted by a suitable coenzyme-dependent dehydrogenase. The same applies for the determination of the enzyme activity of such dehydrogenases.

A further subject matter of the invention is a so-called test kit for carrying out the enzyme or analyte determination. The kit is essentially composed of two reagents. The first reagent comprises—in the case that the activity of a dehydrogenase is determined—a hydrogen-transferring analyte (substrate) in a suitable system buffering between pH 8.5 and 10.0. The second reagent contains a coenzyme for hydrogen-transferring enzymes such as for example NAD or NADP and a water-soluble heavy metal salt at a concentration of ca. 1.0 and 60 mM. In addition the second reagent can contain a complexing agent at a concentration of 0.5 to 30 mM. An analogous second reagent should be used in the case that an analyte or substrate is determined such as for example lactate.

Abbreviations:

| | |
|---|---|
| AMP = | 2-amino-2-methyl-1-propanol |
| AMPSO = | 3-[(1,1-dimethyl-2-hydroxylethyl)amino-2-hydroxypropanesulfonic acid |
| bicine = | N,N-bis[2-hydroxyethyl]glycine |
| CAPS = | 3-[(cyclohexylamino]-1-propanesulfonic acid |
| CAPSO = | 3-[cyclohexylamino]-2-hydroxy-1-propane-sulfonic acid |
| CHES = | 2-[N-cyclohexylamino]ethanesulfonic acid |
| MEG = | N-methylglucamine |
| TAPS = | N-Tris[hydroxymethyl]methyl-3-aminopropane-sulfonic acid |
| tricine = | N-Tris[hydroxymethyl]methylglycerol |
| TRIS = | 2-amino-2-(hydroxymethyl)-1,3-propanol |

The invention is elucidated further by the following examples:

EXAMPLE 1

Reagent 1: 390 mmol/l N-methyl glucamine, pH 9.4 (37° C); 60 mmol/l lithium-L-lactate.

Reagent 2: 60 mmol/l NAD(P)+5 mmol/l copper (II) sulfate as a lyophilisate, powder mixture, granulate or aqueous solution.

Incubation temperature: 37±0.1° C.; measurement wavelength 340±2 nm; light path 7 mm;

Preincubation: 5 minutes; lag phase: 2 minutes; measurement period: 2 minutes.

Reagent 1=250 µl; reagent 2=50 µl; sample 7 µl NaCl solution (0.9% w/v).

a) addition of 5 mmol/l copper (II) reagent 2:

| reagent blank value in mA/min | | |
|---|---|---|
| | unstressed | stressed (35° C. 14 days and 42° C. 1 day) |
| NAD (aqueous sol.) | 2.5 | 19.3 |
| NAD + 5 mmol/l Cu(II) (aqueous sol.) | 0.8 | 4.4 | b) addition of 5 mmol/l copper (II)+EDTA to reagient 2:

| reagent blank value in mA/min | | |
|---|---|---|
| | unstressed | stressed (35° C. 14 days and 42° C. 1 day) |
| NAD (aqueous sol.) | 2.5 | 19.3 |
| NAD + 5 mmol/l Cu + 2.5 mmol/l EDTA (aqueous sol.) | 0.8 | 5.0 |

EXAMPLE 2

Reagent 1 and 2 from example 1 were used with the modified concentrations of copper(II) and cobalt (II) sulfate described in the following.

a) addition of 0–60 mmol/l copper (II) reagent 2:

| reagent blank value in mA/min NAD aqueous solution addition of x mmol/l Cu (II) | | |
|---|---|---|
| | unstressed | stressed (1 day 42° C.) |
| 0 mmol/l Cu (II) | 1.6 | 5.3 |
| 20 mmol/l Cu (II) | −0.2 | 0 |
| 40 mmol/l Cu (II) | 0.8 | 1.4 |
| 60 mmol/l Cu (II) | 2.1 | 2 | b) addition of 3 mmol/l cobalt (II) reagent 2:

| reagent blank value in mA/min | | |
|---|---|---|
| | unstressed | stressed (1 day 42° C.) |
| NAD (aqueous sol.) | 2.5 | 19.3 |
| NAD + 3 mmol/l Co (II) (aqueous sol.) | 0.6 | 18.5 | c) addition of 5 mmol/l copper (II) to reagent 2 (NADP) 1. under stress (42° C.)

| | reagent blank value in mA/min | |
|---|---|---|
| | unstressed | stressed (1 day 42° C.) |
| NADP (aqueous sol.) without Cu (II) | −0.1 | 1.4 |
| NADP + 5 mmol/l Cu (aqueous sol.) | −0.8 | −0.6 |

2. Stability without stress (20° C.)

| | blank value [mA] | | |
|---|---|---|---|
| | 0 months | 9 months | 18 months * |
| NADP (aqueous sol.) without Cu (II) | 2.3 | 11.9 | 21.5 |
| NADP + 5 mmol/l Cu(II) (aqueous sol.) | 0.7 | 2.2 | 3.7 |

* extrapolated

What is claimed is:

1. A stabilized coenzyme solution, consisting essentially of
    a heavy metal salt which is water-soluble and has a concentration of about 1 mM to 60 mM, comprising a heavy metal cation and at least one counterion;
    a hydrogen accepting coenzyme having a concentration of about 1.0 mM to about 60 mM; and
    a buffering solution comprising at least one buffer to produce a stabilized coenzyme solution having a pH of at least 8.5.

2. The coenzyme solution of claim 1, wherein the concentration of the heavy metal salt is about 2 mM to about 10 mM.

3. The coenzyme solution of claim 1, wherein the pH of the stabilized coenzyme solution is between about 8.5 and 10.0.

4. The coenzyme solution of claim 1, wherein the coenzyme is selected from the group consisting of nicotinamide adenine dinucleotide (NAD), nicotinamide adenine dinucleotide phosphate (NADP), thioNAD, thioNADP, and nicotinamide hypoxanthine-dinucleotide phosphate.

5. The coenzyme solution of claim 1, wherein the concentration of the coenzyme is about 5.0 mM to about 15 mM.

6. The coenzyme solution of claim 1, further containing a complexing agent.

7. The coenzyme solution of claim 6, wherein the amount of heavy metal salt in the coenzyme colution is greater than the amount of the complexing agent in the coenzyme solution.

8. The coenzyme solution of claim 6, wherein the ratio of the heavy metal salt to the complexing agent is about 2:1.

9. The coenzyme solution of claim 6, wherein the concentration of the complexing agent is about 0.5 mM to about 30 mM.

10. The coenzyme solution of claim 6, wherein the complexing agent is present in the coenzyme solution at a concentration of about 1.0 mM to about 5.0 mM.

11. The coenzyme solution of claim 1, wherein the heavy metal salt is a salt of copper, cobalt, iron, manganese, zinc, nickel, silver or palladium.

12. The coenzyme solution of claim 1, wherein the heavy metal salt is a salt of $Cu^{2+}$ or $Co^{2+}$.

13. The coenzyme solution of claim 6, wherein the complexing agent is a bidentate ligand or a respective salt thereof.

14. The coenzyme solution of claim 13, wherein the complexing agent is selected from the group consisting of ethylene diamine, ethylene diamine-N,N,N,N-tetraacetic acid and corresponding disodium salt thereof, crown ethers and cryptands.

15. The coenzyme solution of claim 1, wherein the ratio of the coenzyme solution to the buffering solution is about 1:5.

16. The coenzyme solution of claim 1, wherein the buffer is selected from the group consisting of N-Tris[hydroxymethyl]methylglycerol, N,N-bis[2-hydroxyethyl]glycine, N-Tris[hydroxymethyl]methyl-3-aminopropane-sulfonic acid, 3-[(1,1-dimethyl-2-hydroxylethyl)amino-2-hydroxypropanesulfonic acid, 2-[N-cyclohexylamino]-2-hydroxy-1-propane-sulfonic acid, 3-[cyclohexylamino]ethanesulfonic acid, 2-amino-2-methyl-1-propanol, 3-[cyclohexylamino]-1-propanesulfonic acid, carbonates of alkaline metal ions, N-methylglucamine, 2-amino-2-(hydroxymethyl)-1,3-propanol, borate buffer, and phosphate buffer.

17. The coenzyme solution of claim 1, wherein the concentration of buffer in the buffering solution is between about 10 mM and about 1000 mM.

18. The coenzyme solution of claim 1, wherein the concentration of buffer in the buffering solution is between about 400 mM and about 600 mM.

19. The coenzyme solution of claims 1, wherein the at least one counterion is selected from the group consisting of sulfate, phosphate, acid residues of carboxylic acids, and halides.

20. The coenzyme solution of claim 1, wherein the heavy metal salt is selected from the group consisting of copper sulfate, cobalt sulfate, copper chloride and cobalt chloride.

21. A lyophilizate prepared by lyophilizing the coenzyme solution of claim 1.

22. A lyophilizate pregared by lyophilizing the coenzyme solution of claim 6.

23. A ready-to-use granulate powder mixture prepared by drying the coenzyme solution of claim 1.

24. A ready-to-use granulate powder mixture prepared by drying the coenzyme solution of claim 6.

25. The coenzyme solution of claim 1, wherein the coenzyme solution is a ready-to-use aqueous solution.

26. The coenzyme solution of claim 6, wherein the coenzyme solution is a ready-to-use aqueous solution.

27. A method for determining a hydrogen-transferring analyte in a sample in the presence of a hydrogen accepting coenzyme, comprising the steps of
    mixing a buffering substance having a pH of about 8.5 to about 10.0 with a dehydrogenase corresponding to the hydrogen-transferring analyte to be determined;
    mixing the buffering substance having the dehydrogenase therein with a stabilized coenzyme solution consisting essentially of a hydrogen accepting coenzyme and a heavy metal salt which is water-soluble, to obtain a mixture; and
    mixing the hydrogen-transferring analyte to be determined with the mixture; and
    determining the hydrogen-transferring analyte.

28. The method of claim 27, wherein the sample is a body fluid.

29. The method of claim 28, wherein the sample is blood.

30. The method of claim 27, wherein the hydrogen transfering analyte is lactate, the dehydrogenase is lactate dehydrogenase, and the determination is performed at a temperature of about 37° C.

31. The method of claim 30, wherein about 70 U/l to about 500 U/l of the lactate dehydrogenase is added to the buffering substance.

32. The method of claim 30, wherein about 110 U/l to about 220 U/l of the lactate dehydrogenase is added to the buffering substance.

33. The method of claim 27, wherein the hydrogen transfering analyte is selected from the group consisting of glutamate, ammonia, alcohol, glyceraldehyde-3-phospate, and glucose.

34. The method of claim 27, wherein the coenzyme solution further comprises a complexing agent.

35. A method for determining the enzyme activity of a dehydrogenase in a sample, in the presence of a hydrogen accepting coenzyme, comprising the steps of
   mixing a buffering substance having a pH of about 8.5 to about 10.0 with hydrogen-transferring analyte corresponding to the dehydrogenase to be determined;
   mixing the buffered substance having the hydrogen-transferring analyte therein with a stabilized coenzyme solution consisting essentially of a hydrogen accepting coenzyme and a heavy metal salt which is water-soluble, to obtain a mixture;
   mixing the dehydrogenase to be determined with the mixture; and,
   determining the enzyme activity of the dehydrogenase.

36. The method of claim 35, wherein the enzyme to be determined is lactate dehydrogenase, the hydrogen-transferring analyte is lactate, and the determination is carried out at a pH of about 9.4 and a temperature of about 37° C.

37. The method of claim 35, wherein the coenzyme solution further comprises a complexing agent.

38. A test kit for the determination of a hydrogen transfering analyte in a sample, consisting essentially of
   a first reagent consisting essentially of a dehydrogenase in a buffering system with pH level of about 8.5 to about 10.0; and
   a second reagent consisting essentially of a coenzyme for hydrogen-transferring enzymes, and a water-soluble heavy metal salt at a concentration of about 1.0 mM to about 60 mM.

39. The test kit as in claim 38, wherein the second reagent further comprises a complexing agent at a concentration of between about 0.5 to about 30 mM.

40. The test kit as in claim 38, wherein the first reagent and the second reagent are contained in separate packages.

41. A test kit for the determination of an enzyme activity of a dehydrogenase in a sample, consisting essentially of a first reagent consisting essentially of a hydrogen-transfering analyte in a buffering system having pH level of about 8.5 to about 10.0; and
   a second reagent consisting essentially of a coenzyme for hydrogen-transfering enzymes, and a water-soluble heavy metal salt at a concentration of about 1.0 mM to about 60 mM.

42. The test kit as in claim 41, wherein the second reagent further comprises a complexing agent at a concentration of about 0.5 mM to about 30 mM.

43. The test kit as in claim 41, wherein the coenzyme is selected from the group consisting of nicotinamide adenine dinucleotide (NAD), nicotinamide adenine dinucleotide phosphate (NADP), thioNAD, thioNADP and nicotinamide hypoxanthine-dinucleotide phosphate.

44. The test kit as in claim 41, wherein the first reagent and the second reagent are contained in separate packages.

45. The method of claim 35, wherein the dehydrogenase is a dehydrogenase for a hydrogen transferring analyte selected from the group consisting of glutamate, ammonia, alcohol, glyceraldehyde-3-phosphate, and glucose.

46. A stabilized coenzyme solution, consisting essentially of
   about 1 mM to about 60 mM of at least one water-soluble salt of silver or palladium with at least one counterion; and
   a hydrogen accepting coenzyme having a concentration of about 1.0 mM to about 60 mM.

47. The coenzyme solution of claim 46, wherein the pH of the stabilized coenzyme solution is between about 8.5 and about 10.0.

48. The coenzyme solution of claim 46, wherein the concentration of the salt of silver or palladium is about 2 mM to about 10 mM.

49. The coenzyme solution of claim 46, wherein the coenzyme is selected from NAD, NADP, thioNAD, thioNADP and nicotinamide hypoxanthine dinucleotide phosphate.

50. The coenzyme solution of claim 46, wherein the concentration of the coenzyme is about 5 mM to about 15 mM.

51. The coenzyme solution of claim 6, wherein the complexing agent is selected from the group consisting of ethylene diamine, ethylene diamine-N,N,N,N-tetraacetic acid, corresponding disodium salt thereof, crown ethers and cryptands.

52. The method of claim 34, wherein the complexing agent is selected from the group consisting of ethylene diamine, ethylene diamine-N,N,N,N-tetraacetic acid, corresponding disodium salt thereof, crown ethers and cryptands.

53. The test kit of claim 42, wherein the complexing agent is selected from the group consisting of ethylene diamine, ethylene diamine-N,N,N,N-tetraacetic acid, corresponding disodium salt thereof, crown ethers and cryptands.

54. The method of claim 37, wherein the complexing agent is selected from the group consisting of ethylene diamine, ethylene diamine-N,N,N,N-tetraacetic acid, corresponding disodium salt thereof, crown ethers and cryptands.

55. The test kit of claim 39, wherein the complexing agent is selected from the group consisting of ethylene diamine, ethylene diamine-N,N,N,N-tetraacetic acid, corresponding disodium salt thereof, crown ethers and cryptands.

56. A stabilized coenzyme solution, consisting of
   a heavy metal salt which is water-soluble and has a concentration of about 1 mM to 60 mM, comprising a heavy metal cation and at least one counterion;
   a hydrogen accepting coenzyme having a concentration of about 1.0 mM to about 60 mM; and a buffering solution comprising at least one buffer to produce a stabilized coenzyme solution having a pH of at least 8.5.

57. The coenzyme solution of claim 56, wherein the concentration of the heavy metal salt is about 2 mM to about 10 mM.

58. The coenzyme solution of claim 56, wherein the pH of the stabilized coenzyme solution is between about 8.5 and 10.0.

59. The coenzyme solution of claim 56, wherein the coenzyme is selected from the group consisting of nicotinamide, adeninine dinucleotide (NAD), nicotinamide adenine dinucleotide phosphate (NADP), thioNAD, thioNADP, and nicotinamide hypoxanthine-dinucleotide phosphate.

\* \* \* \* \*